(12) United States Patent
Narula et al.

(10) Patent No.: US 8,461,100 B1
(45) Date of Patent: Jun. 11, 2013

(54) DECENAL MIXTURES AND THEIR USE IN PERFUME COMPOSITIONS

(75) Inventors: Anubhav P. S. Narula, Hazlet, NJ (US); Edward Mark Arruda, Easton, PA (US); Franc T. Schiet, Naarden (NL)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 13/369,420

(22) Filed: Feb. 9, 2012

Related U.S. Application Data

(60) Provisional application No. 61/579,642, filed on Dec. 22, 2011.

(51) Int. Cl.
*A61K 8/33* (2006.01)

(52) U.S. Cl.
USPC .......... 512/25; 512/1; 512/5; 512/26; 512/27; 424/401

(58) Field of Classification Search
USPC .......................... 512/1, 5, 25, 26, 27; 424/401
See application file for complete search history.

(56) References Cited

U.S. PATENT DOCUMENTS

| 5,843,881 A | 12/1998 | Dubois et al. |
| 7,767,640 B2 | 8/2010 | Finke et al. |
| 7,846,886 B2 | 12/2010 | Oertling et al. |
| 2011/0142776 A1 | 6/2011 | Womack et al. |

OTHER PUBLICATIONS

Masanetz, et al., "Hay-Like Off-Flavour of Dry Parsley" Z. Lebensm. Unters. Forsch. (1998) 206:114-120.

*Primary Examiner* — Gina C Justice
(74) *Attorney, Agent, or Firm* — Elizabeth M. Quirk; XuFan Tseng; Joseph F. Leightner

(57) ABSTRACT

The present invention relates to a novel decenal mixture and the incorporation and use of this mixture as a fragrance material. The novel decenal mixture contains decenals that are represented by the formula set forth below:

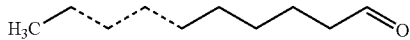

wherein the broken line represents one double bond and two single bonds.

11 Claims, No Drawings

DECENAL MIXTURES AND THEIR USE IN PERFUME COMPOSITIONS

STATUS OF RELATED APPLICATIONS

This application claims priority to U.S. provisional patent application Ser. No. 61/579,642, filed Dec. 22, 2011, the contents of which are incorporated herein by reference.

FIELD OF THE INVENTION

The present invention relates to novel decenal mixtures and the incorporation and use of these mixtures as fragrance materials.

BACKGROUND OF THE INVENTION

There is an ongoing need in the fragrance industry to provide chemicals with strong odors so that less fragrance is needed to accomplish the desired odor effect. This, therefore, gives perfumers and other persons the freedom to create new fragrances for perfumes, colognes and personal care products without the limitation of cost. In addition to odor strength, practical considerations such as the scale of synthesis operation may also determine the applicability of identified fragrance molecules in commercial use. However, whether the production of a given fragrance molecule can be carried out at a commercial scale is sometimes unpredictable. For these reasons, continuous effort has been made in fragrance industry to investigate and develop economical processes for making fragrance molecules that possess high strength.

One skilled person recognizes and appreciates the combinations of existing fragrance ingredients that possess superior effect when compared to individual ingredients. Such combinations are considered unexpected and inventive (See, for example, U.S. Pat. No. 7,767,640 and U.S. Pat. No. 7,846,886).

Dec-6-enal is identified as a flavorant in dry parsley (See, Masanetz et al.). Dec-7-enal is employed to reduce the alcohol odor and alcohol sting, but it acts differently from a traditional perfume, wherein a traditional perfume overpowers the alcohol odor or sting by making compositions smell like the perfume (See, U.S. Pat. No. 5,843,881). Dec-8-enal falls under a generic structure that is disclosed as having potential fragrance use (See, U.S. Publication No. 2011/0142776). However, the generic structure as taught covers a wide range of compounds and the synthetic method as described cannot lead to the synthesis of dec-8-enal.

Thus, dec-6-enal, dec-7-enal, and dec-8-enal were each individually reported since early 1990's with various flavor and fragrance properties. They were extracted from natural resources or synthesized via methods that required multi-steps and suffered from long reaction times leading to complex and expensive procedures. To date, none of dec-6-enal, dec-7-enal, and dec-8-enal has achieved commercial importance as a fragrance material. More importantly, nothing set forth in the prior art discloses a mixture of dec-6-enal, dec-7-enal, and dec-8-enal having specified ratios.

The present invention has discovered a convenient and economical process that provides a novel mixture of dec-6-enal, dec-7-enal, and dec-8-enal. The present invention has further surprisingly and unexpectedly discovered that this novel decenal mixture, only when in specified mixing ratios, possesses desirable fragrance properties of high strength that are suitable for fragrance application.

SUMMARY OF THE INVENTION

The present invention provides a novel decenal mixture and its unexpected advantageous use in enhancing, improving or modifying the fragrance of perfumes, colognes, toilet water, fabric care products, personal products and the like.

More specifically, the novel decenal mixture contains decenals that are represented by Formula I set forth below:

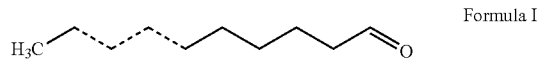

Formula I wherein the broken line represents one double bond and two single bonds.

Another embodiment of the present invention relates to a fragrance composition comprising the novel mixture provided above.

Another embodiment of the present invention relates to a fragrance product comprising the novel mixture provided above.

Another embodiment of the present invention relates to a method of improving, enhancing or modifying a fragrance formulation through the addition of an olfactory acceptable amount of the novel mixture provided above.

Another embodiment of the present invention relates to a method of making the novel mixture provided above.

These and other embodiments of the present invention will be apparent by reading the following specification.

DETAILED DESCRIPTION OF THE INVENTION

The decenals of the present invention may be represented by the following structures:

Formula II

Formula III

Formula IV

Those with the skill in the art will appreciate that

Formula II is dec-6-enal;

Formula III is dec-7-enal; and

Formula IV is dec-8-enal.

The present invention relates to a mixture of dec-6-enal, dec-7-enal, and dec-8-enal.

The present invention further relates to a mixture of dec-6-enal (~8-22% by weight), dec-7-enal (~20-43%), and dec-8-enal (~35-59%) that possesses desirable and useful fragrance properties.

The decenals of the present invention can be prepared from 9-decenol (Rosalva, commercially available at International Flavors & Fragrances Inc.) according to the reaction scheme below, the details of which are specified in the Examples. Materials were purchased from Aldrich Chemical Company unless noted otherwise.

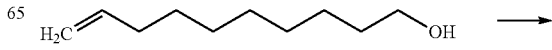

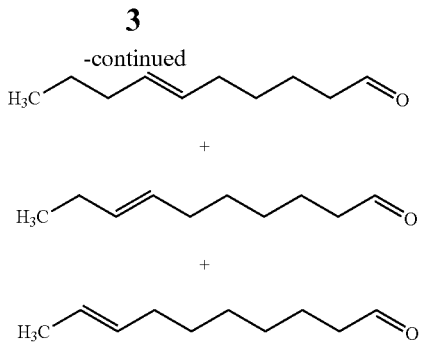

Additionally, specific ratios of dec-6-enal (Formula II), dec-7-enal (Formula III), and dec-8-enal (Formula IV) were obtained.

It has been surprisingly and unexpectedly found that there exist criticality to the mixing ratios of dec-6-enal, dec-7-enal, and dec-8-enal. Specifically, only a decenal mixture containing dec-6-enal (~8-22% by weight), dec-7-enal (~20-43%), and dec-8-enal (~35-59%) has been found to possess desirable and useful fragrance properties of high strength while a mixing ratio outside the specified ranges will cause off-notes and render the decenal mixture unsuitable for fragrance use. Thus, the present invention relates to the surprising and unexpected discovery of the criticality of the mixing ratios in the dec-6-enal, dec-7-enal, and dec-8-enal mixture.

Those with skill in the art will recognize that, if needed, the isomeric products obtained as described above can be further separated using techniques known to those with skill in the art. Suitable techniques include, for example, distillation and chromatography such as high performance liquid chromatography, referred to as HPLC, particularly silica gel chromatograph, and gas chromatography trapping known as GC trapping. Yet, commercial products are mostly offered as isomeric mixtures.

The use of the decenal mixtures of the present invention is widely applicable in current perfumery products, including the preparation of perfumes and colognes, the perfuming of personal care products such as soaps, shower gels, and hair care products, fabric care products, air fresheners, and cosmetic preparations. The present invention can also be used to perfume cleaning agents, such as, but not limited to detergents, dishwashing materials, scrubbing compositions, window cleaners and the like.

In these preparations, the decenal mixtures of the present invention can be used alone or in combination with other perfuming compositions, solvents, adjuvants and the like. The nature and variety of the other ingredients that can also be employed are known to those with skill in the art. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The decenal mixtures of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1,3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylbicyclo[2.2.1]hept-2-yl)oxy]exo-1-propanol (Bornafix), 1,2,3,5,6,7-hexahydro-1,1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexylon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methylpentyl)cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl) pent-1-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo[7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl)cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl)oxy]-3-hexene (Vivaldie).

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising the decenal mixtures of the present invention. The fragrance formulation of the present invention comprises the decenal mixtures of the present invention and further a complementary fragrance compound as defined above.

The term "fragrance product" means a consumer product that adds a fragrance or masks a malodor. Fragrance products may include, for example, perfumes, colognes, personal care products such as soaps, shower gels, and hair care products, fabric products, air fresheners, cosmetic preparations, and perfume cleaning agents such as detergents, dishwashing materials, scrubbing compositions, and window cleaners. The fragrance product of the present invention is a consumer product that contains the decenal mixtures of the present invention. The fragrance product of the present invention contains the decenal mixtures of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

Olfactory acceptable amount is understood to mean the amount of compound in perfume compositions the individual component will contribute to its particular olfactory characteristics, but the olfactory effect of the perfume composition will be the sum of the effects of each of the perfumes or fragrance ingredients. Thus the decenal mixtures of the invention can be used to alter the aroma characteristics of the perfume composition, or by modifying the olfactory reaction contributed by another ingredient in the composition. The amount will vary depending on many factors including other ingredients, their relative amounts and the effect that is desired.

The amount of the decenal mixtures of the present invention employed in a fragrance formulation varies from about 0.005 to about 70 weight percent, preferably from 0.005 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the decenal mixtures of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation these ingredients provide powerful, clean, aldehydic, crispy, green, ambrette seed like, sweet, bright, and melon notes to make the fragrance formulation more desirable and noticeable, and add the perception of value. The odor qualities found in this material assist in beautifying and enhancing the finished accord as well as improving the performance of the other materials in the fragrance.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, g is understood to be gram, mg is understood to be milligram, and mmHg be millimeters (mm) of mercury (Hg). IFF as used in the examples is understood to mean International Flavors & Fragrances Inc., New York, N.Y., USA.

Example I

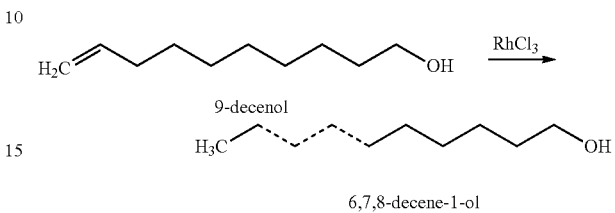

Preparation of 6,7,8-Decene-1-ol (Mixture of 6-Decene-1-ol, 7-Decene-1-ol, and 8-Decene-1-ol)

A reaction flask was charged with toluene (500 g), 9-decenol (Rosalva) (500 g), and rhodium trichloride ($RhCl_3$) (1.25 g). Water (2 g) was added. The reaction mixture was heated with stirring to about 65-80° C. The reaction mixture was heated for about 20 hours till a steady state of 6,7,8-decene-1-ol isomers was reached. The reaction mixture was then cooled. The organic layer was transferred to a rush-over distillation flask and Primol oil (15 g) was added. Toluene was then removed at atmospheric pressure. The crude product was distilled to afford 6,7,8-decene-1-ol (463 g) having a boiling point of 98° C. at a pressure of 3.2 mmHg. The broken line in the above formula of 6,7,8-decene-1-ol represents one double bond and two single bonds.

6,7,8-Decene-1ol was described as having aldehydic, green, floral, rosy, and waxy notes.

Example II

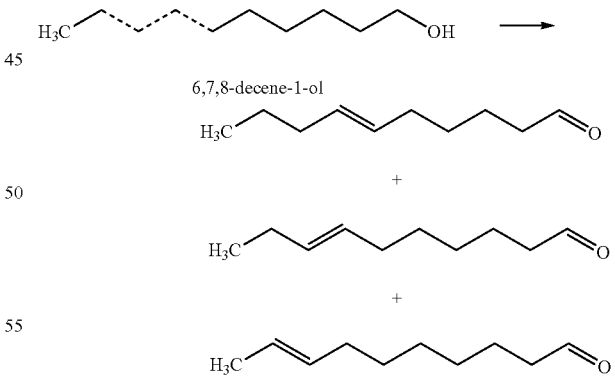

Preparation of Dec-6-enal (Formulas II), Dec-7-enal (Formulas III), and Dec-8-enal (Formulas IV)

A reaction flask was charged with Primol oil (100 g) and Pricat catalyst (25 g, commercially available at Johnson Matthey Catalysts). The reaction mixture was heated with stirring to about 250-290° C. The mixture of 6,7,8-decene-1 ol (238 g, synthesized as above in EXAMPLE I) was then added slowly while the temperature was maintained at about 290-295° C. The reaction was vented properly during the reaction. After the reaction was completed, the reaction mixture was transferred into a distillation flask and further fractional distillation afforded the mixture of Formulas II, III, and IV (141 g) having a boiling point of 80° C. at a pressure of 6.8-7.8 mmHg. It was surprisingly found that the double bond position along the carbon chain could be specified and only careful control of the reaction conditions in both steps (EXAMPLEs I and II) would lead to the desired decenal isomers.

Dec-6-enal $^1$H NMR: 9.76 ppm (br, 1H), 5.30-5.50 ppm (m, 2H), 2.42 ppm (t, 2H, J=7.4 Hz), 1.90-2.13 ppm (m, 4H), 1.54-1.73 ppm (m, 2H), 1.20-1.45 ppm (m, 4H), 0.88 ppm (t, 3H, J=7.4 Hz)

Dec-7-enal $^1$H NMR: 9.76 ppm (br, 1H), 5.30-5.50 ppm (m, 2H), 2.42 ppm (t, 2H, J=7.4 Hz), 1.90-2.13 ppm (m, 4H), 1.54-1.73 ppm (m, 4H), 1.20-1.45 ppm (m, 2H), 0.96 ppm (t, 3H, J=7.4 Hz)

Dec-8-enal $^1$H NMR: 9.76 ppm (br, 1H), 5.30-5.50 ppm (m, 2H), 2.42 ppm (t, 2H, J=7.4 Hz), 1.90-2.13 ppm (m, 2H), 1.63 ppm (br, s, 3H), 1.54-1.73 ppm (m, 2H), 1.20-1.45 ppm (m, 6H)

Example III

Preparation and Evaluation of Dec-6-enal, Dec-7-enal, and Dec-8-enal Mixture of Different Ratios The decenal mixture (synthesized as above in EXAMPLE II) was further carefully distilled through a GOODLOE column with high theoretical plates to afford a series of decenal mixture of different mixing ratios.

The following specific mixture samples were evaluated for odor properties:

| | Decenal Mixture (% by weight) | | | |
|---|---|---|---|---|
| Sample | Dec-6-enal | Dec-7-enal | Dec-8-enal | Odor Profile |
| 1 | 3 | 46 | 51 | Off notes, too lactonic |
| 2 | 2 | 33 | 65 | Off notes, too fruity and too coconut |
| 3 | 27 | 43 | 30 | Dirty off notes, solventy, and phenolic |
| 4 | 20 | 25 | 55 | Strong, clean, aldehydic, and crispy |
| 5 | 22 | 20 | 58 | Strong, clean, aldehydic, crispy, and slightly green |
| 6 | 9 | 38 | 53 | Strong, clean, aldehydic, crispy, slightly green, bright, and melon |
| 7 | 22 | 43 | 35 | Strong, clean, aldehydic, crispy, green, ambrette seed-like, and slightly sweet |
| 8 | 12 | 31 | 47 | Powerful, very clean, aldehydic, crispy, green, ambrette seed-like, sweet, bright, and melon |
| 9 | 19 | 33 | 40 | Strong, clean, aldehydic, crispy, slightly green, and slightly sweet |
| 10 | 15 | 33 | 43 | Strong, clean, aldehydic, crispy, slightly green, and slightly sweet |

The above evaluation yielded unexpected finding, samples 4-10 were surprisingly superior to samples 1, 2, and 3. There was criticality to the mixing ratios of dec-6-enal, dec-7-enal, and dec-8-enal. Specifically, only a decenal mixture containing dec-6-enal (~8-22% by weight), dec-7-enal (~20-43%), and dec-8-enal (~35-59%) were found to possess desirable fragrance properties of high strength while a mixing ratio outside the defined ranges caused off-notes which rendered the decenal mixture unsuitable for fragrance use. Thus, the present invention made surprising and unexpected discovery of the criticality of the mixing ratios in dec-6-enal, dec-7-enal, and dec-8-enal mixture.

Example IV

The fragrance formula exemplified as follows demonstrated that the addition of the mixture of dec-6-enal (22%), dec-7-enal (43%), and dec-8-enal (35%) (Sample 7 as described in EXAMPLE III) provided clean, aldehydic, crispy, green, ambrette seed-like, and slightly sweet characters to the fragrance formula.

| Ingredient | Parts (g) |
|---|---|
| Benzophenone | 100 |
| Cinnamic Alcohol | 50 |
| Damascone, Delta | 5 |
| Decanol, n- | 30 |
| Dimethyl Benzyl Carbinyl Acetate | 50 |
| Diphenyl Oxide | 20 |
| Dodecanol, n- | 15 |
| Ethyl Methyl Phenyl Glycidate | 5 |
| Eugenol | 10 |
| Geraniol | 60 |
| Guaiacwood Oil | 20 |
| Ionone Alpha | 10 |
| Iso E Super ® | 60 |
| Methyl Ionone Gamma | 65 |
| Octanol, n- | 10 |
| Phenoxanol ® | 200 |
| Phenyl Acetaldehyde Dimethyl Acetal | 7 |
| Phenyl Ethyl Alcohol | 100 |
| Phenyl Methyl Carbinyl Acetate | 20 |
| Rose Oxide | 5 |
| Vertenex ® | 150 |
| Decenal Mixture (Sample 7) | 8 |
| Total | 1000 |

Example V

The fragrance formula exemplified as follows demonstrated that the addition of the mixture of dec-6-enal (15%), dec-7-enal (33%), and dec-8-enal (43%) (Sample 10 as described in EXAMPLE III) provided clean, aldehydic, crispy, slightly green, and slightly sweet characters to the fragrance formula.

| Ingredient | Parts (g) |
| --- | --- |
| Agrumea (Schiff base of Triplal ® and Methyl Anthranilate) | 10 |
| Allyl Cyclohexyl Proprionate | 10 |
| Ambroxan | 2 |
| Benzophenone | 5 |
| Cyclacet ® | 40 |
| Cyclaprop ® | 40 |
| Damascone Delta | 8 |
| Dihydro Myrcenol | 65 |
| Dimethyl Benzyl Carbinyl Acetate | 10 |
| Diola | 4 |
| Diphen Oxide | 2 |
| Dodecanal, n- | 2 |
| Eugenol | 4 |
| Geraniol | 60 |
| Hexenyl Isobutyrate, Cis-3- | 6 |
| Hexyl Cinnamic Aldehyde | 70 |
| Ionone Alpha | 4 |
| Iso E Super ® | 100 |
| Koavone ® | 20 |
| Lavandin Oil Grosso | 20 |
| Methyl Beta Naphtyl Ketone | 2 |
| Methyl Ionone Gamma | 30 |
| Nerol | 30 |
| Petitgrain Oil | 2 |
| Phenoxanol ® | 20 |
| Phenoxy Ethyl Isobutyrate | 8 |
| Phenyl Ethyl Alcohol | 50 |
| Prenyl Acetate | 12 |
| Rose Oxide | 2 |
| Sage Oil French | 2 |
| Salicynalva | 90 |
| Sanjinol | 4 |
| Phenyl Methyl Carbinyl Acetate | 15 |
| Tetrahydro Myrcenol | 50 |
| Trimofix O | 5 |
| Undecalactone Gamma | 20 |
| Undecavertol | 5 |
| Verdox | 70 |
| Vertenex ® HC | 50 |
| Vertofix ® Coeur | 30 |
| Vertoliff | 12 |
| Violiff | 5 |
| Decenal Mixture (Sample 10) | 4 |
| Total | 1000 |

What is claimed is:

1. A fragrance formulation comprising a mixture of dec-6-enal, dec-7-enal, and dec-8-enal, wherein the mixture contains about 8-22% by weight of dec-6-enal, about 20-43% by weight of dec-7-enal, and about 35-59% by weight of dec-8-enal.

2. The fragrance formulation of claim 1 incorporated into a product selected from the group consisting of a perfume, a cologne, toilet water, a cosmetic product, a personal care product, a fabric care product, a cleaning product, and an air freshener.

3. The fragrance formulation of claim 2, wherein the cleaning product is selected from the group consisting of a detergent, a dishwashing composition, a scrubbing compound, and a window cleaner.

4. The fragrance formulation of claim 2, wherein the mixture is incorporated at a level of from about 0.005 to about 50 weight percent of the product.

5. The fragrance formulation of claim 2, wherein the mixture is incorporated at a level of from about 0.5 to about 25 weight percent of the product.

6. The fragrance formulation of claim 2, wherein the mixture is incorporated at a level of from about 1 to about 10 weight percent of the product.

7. A method of improving, enhancing or modifying a fragrance formulation through the addition of an olfactory acceptable amount of a mixture of dec-6-enal, dec-7-enal, and dec-8-enal, wherein the mixture contains about 8-22% by weight of dec-6-enal, about 20-43% by weight of dec-7-enal, and about 35-59% by weight of dec-8-enal.

8. The method of claim 7, wherein the olfactory acceptable amount is from about 0.005 to about 50 weight percent of the fragrance formulation.

9. The method of claim 7, wherein the olfactory acceptable amount is from about 0.5 to about 25 weight percent of the fragrance formulation.

10. The method of claim 7, wherein the olfactory acceptable amount is from about 1 to about 10 weight percent of the fragrance formulation.

11. A fragrance product comprising a mixture of dec-6-enal, dec-7-enal, and dec-8-enal, wherein the mixture contains about 8-22% by weight of dec-6-enal, about 20-43% by weight of dec-7-enal, and about 35-59% by weight of dec-8-enal.

* * * * *